United States Patent [19]
Kobayashi

[11] Patent Number: 5,300,964
[45] Date of Patent: Apr. 5, 1994

[54] FUNDUS CAMERA

[75] Inventor: Kazunobu Kobayashi, Yokohama, Japan

[73] Assignee: Canon Kabushiki Kaisha, Tokyo, Japan

[21] Appl. No.: 866,770

[22] Filed: Apr. 9, 1992

[30] Foreign Application Priority Data

Apr. 16, 1991 [JP] Japan .................. 3-110935

[51] Int. Cl.$^5$ .............................................. A61B 3/14
[52] U.S. Cl. .................... 351/207; 351/206; 354/62
[58] Field of Search ............... 351/206, 221, 207, 216, 351/211; 354/62

[56] References Cited

U.S. PATENT DOCUMENTS

| | | | |
|---|---|---|---|
| 4,068,932 | 1/1978 | Ohta et al. | 354/62 |
| 4,149,787 | 4/1979 | Kobayashi et al. | 351/206 |
| 4,162,827 | 7/1979 | Ito | 351/207 |
| 4,283,124 | 8/1981 | Matsumura | 351/206 |
| 4,690,525 | 9/1987 | Kobayashi et al. | 351/206 |
| 4,991,584 | 2/1991 | Kobayashi et al. | 128/648 |

Primary Examiner—William L. Sikes
Assistant Examiner—Hung Xuan Dang
Attorney, Agent, or Firm—Fitzpatrick, Cella, Harper & Scinto

[57] ABSTRACT

A fundus camera includes a light source for observation, and an illuminating optical system having a predetermined illuminating optical axis. The light source for observation illuminates a fundus of an eye via the illiminating optical system. The camera further includes an observation optical system disposed so as to be able to observe the fundus illuminated by the light source for observation, a photographing light source for illiminating the fundus during a photographing operation and disposed on the illiminating optical axis of the illiminating optical system, a photographing system for photographing the fundus illuminated by the photographing light source, and a reflecting member disposed between the light source for observation and the photographing light source on the illiminating optical axis so as to reflect light from the photographing light source in the direction of the fundus during illumination by the photographing light source. The reflecting member is retractable from the illiminating optical axis.

12 Claims, 2 Drawing Sheets

FUNDUS CAMERA

BACKGROUND OF THE INVENTION

1. Field of the Invention

This invention relates to a fundus camera which includes an illuminating means comprising a reflecting member.

2. Description of the Related Art

In a conventional fundus camera in which a light source for observation and a photographing light source are disposed on the same optical axis, an observation operation or a photographing operation is performed by illuminating the pupil of an eye whose area is restricted with illuminating light, and separating light reflected by the fundus of the eye.

In the above-described conventional approach, however, in order to obtain sufficiently-intense light reflected by the fundus, the incident light must have a high intensity. Therefore, it is necessary to use a high-power power supply for increasing the brightness of a light source, and a light source which can withstand high brightness. Hence, the size of the power supply increases, and the production cost also increases. In addition, a particular expensive material must be used for a light source which can be lit at high brightness, and the life of the light source is shortened.

SUMMARY OF THE INVENTION

It is an object of the present invention to overcome the problems of the prior art.

It is another object of the present invention to provide a simple fundus camera which produces high intensity light without the necessity of using a high power supply and without shortening the life of the light source.

According to one aspect, the invention which achieves these objectives relates to a fundus camera for illuminating the fundus of an eye to be inspected which disposes a photographing light source on an illuminating optical axis from a light source for observation to the eye and which provides a reflecting member for reflecting photographing light traveling toward the light source for observation in the direction of the eye, and which can retract outside of the optical path between the light source for observation and the photographing light source. The reflecting member is disposed between the two light sources during a photographing operation.

The reflecting member for reflecting photographing light in the direction of the eye is disposed between the two light sources only during the photographing operation for producing a photograph or a television image, and the light source is retracted outside the optical path when the photographing operation is not performed.

According to still another aspect, the present invention which achieves these objectives relates to a fundus camera, comprising a light source for observation, an illuminating optical system having a predetermined illuminating optical axis, the light source for observation illuminating a fundus of an eye via the illuminating optical system, an observation optical system disposed so as to be able to observe the fundus illuminated by the light source for observation, a photographing light source for illuminating the fundus during a photographing operation, the photographing light source being disposed on the illuminating optical axis of the illuminating optical system, a photographing system for photographing the fundus illuminated by the photographing light source, and a reflecting member disposed between the light source for observation and the photographing light source on the illuminating optical axis so as to reflect light from the photographing light source in the direction of the fundus during illumination by the photographing light source. The reflecting member is retractable from the illuminating optical axis between the light source for observation and the photographing light source.

In one embodiment, the reflecting member is rotatable substantially around the light source for observation or the photographing light source. In another embodiment, the reflecting member is configured so as to provide reflecting surfaces on both sides thereof. In this embodiment, the reflecting member is disposed between the photographing light source and the light source for observation during illumination of the fundus during the photographing operation by the photographing light source. In this embodiment, the reflecting member is disposed at a position opposite to the direction of illumination of the light source for observation during observation of the fundus by the observation optical system.

The camera can further comprise an actuator for inserting the reflecting member between the photographing light source and the light source for observation. In this embodiment the photographing light source illuminates the fundus while the reflecting member is linked with the actuator.

The camera can further comprise a detector for confirming the insertion of the reflecting member between the photographing light source and the light source for observation. In this embodiment, the photographing light source can illuminate the fundus after the detector has detected the insertion of the reflecting member between the photographing light source and the light source for observation.

The reflecting member can include, in one embodiment, a concave spherical reflecting surface. In another embodiment, the reflecting member includes a plane-like reflecting surface. In this embodiment, the illuminating optical system includes an optical member for illuminating the plane-like reflecting surface while converting light from the photographing light source into parallel light beams when the reflecting member is inserted between the photographing light source and the light source for observation.

According to another aspect, the present invention which achieves these objectives relates to an ophthalmic photographing apparatus comprising a light source for observation, an illuminating optical system having a predetermined illuminating optical axis, the light source for observation illuminating a predetermined portion of an eye to be inspected via the illuminating optical system, an observation optical system disposed so as to be able to observe the predetermined portion of the eye illuminated by the light source for observation, a photographing light source for illuminating the predetermined portion of the eye during a photographing operation, the photographing light source being disposed on the illuminating optical axis of the illuminating optical system, a photographing system for photographing the predetermined portion of the eye illuminated by the photographing light source, and a reflecting member disposed between the light source for observation and the photographing light source on the illuminating optical axis so as to reflect light from the photographing light source in the direction of the eye during illumination by the photographing light source. The reflecting member is retractable from the illuminating optical axis between the light source for observation and the photographing light source. The apparatus can further comprise an actuator for inserting the reflecting member between the photographing light source and the light source for observation. In this embodiment, the photographing light source illuminates the predetermined portion of the eye while the reflecting member is linked with the actuator.

The foregoing and other objects and features of the present invention will become more apparent from the following description of the preferred embodiments of the present invention when taken in conjunction with the drawings.

DESCRIPTION OF THE PREFERRED EMBODIMENTS

Preferred embodiments of the present invention will now be explained in detail with reference to the drawings.

Figure 1:
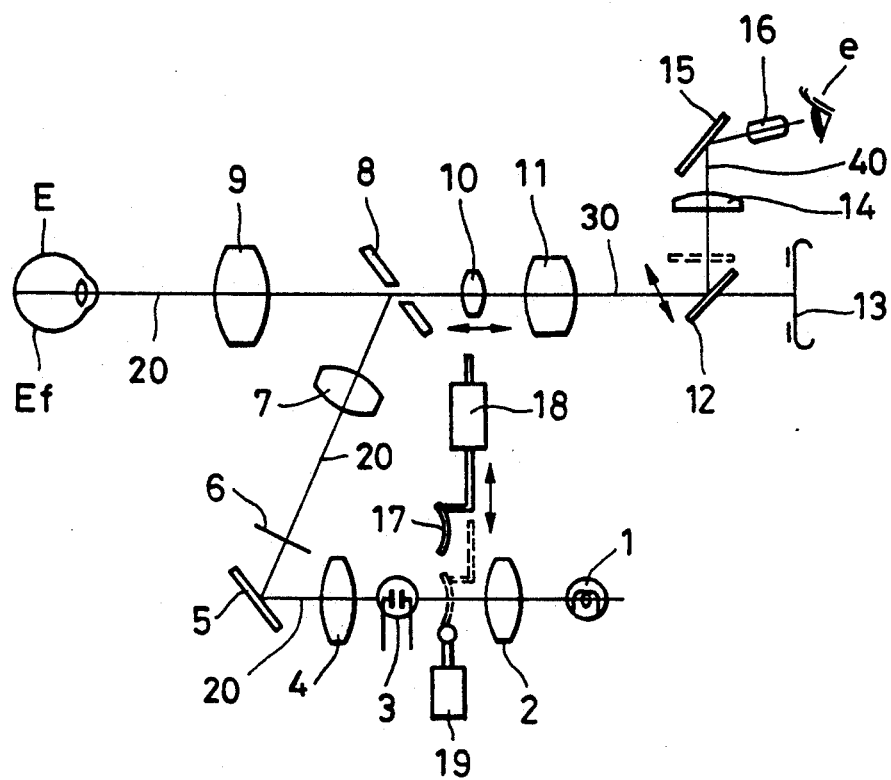
FIG. 1 is a schematic diagram showing the configuration of a fundus camera according to a first embodiment of the present invention.

FIG. 1 is a schematic diagram showing the configuration of a mydriatic fundus camera according to a first embodiment of the present invention. A condenser lens 2, a photographing light source 3 comprising a flash tube, a condenser lens 4, a mirror 5, a ring slit 6 having an annular aperture, a relay lens 7, a mirror 8 having an aperture in its center, and an objective lens 9 are arranged on an optical path 20 from a light source 1 for observation, which emits a visible light beam by lighting a filament lamp, to an eye E to be inspected. A light source 1 for observation and the photographing light source 3 are substantially conjugate with respect to the condenser lens 2, the photographing light source 3 and the ring slit 6 are substantially conjugate with respect to the condenser lens 4, the ring slit 6 and the mirror 8 having the aperture are substantially conjugate with respect to the relay lens 7, and the mirror 8 having the aperture and the vicinity of the pupil of the eye E are substantially conjugate with respect to the objective lens 9. A focusing lens 10, a photographing lens 11, a movable mirror 12 and a film 13 are sequentially arranged on an optical path 30 behind the mirror 8 having the aperture. A field lens 14, a mirror 15 and an eyepiece lens 16 are arranged on an optical path 40 in the direction of reflection of the movable mirror 12. A reflecting member 17 comprising a concave mirror is disposed between the condenser lens 2 and the photographing light source 3 so as to be insertable in the optical path 20. The reflecting member 17 is driven by a solenoid 18, serving as a driving means, and insertion of the reflecting member 17 within the optical path 01 is detected by a microswitch 19.

During observation operation, the light source 1 for observation is lit. Light for observation passes through the lens 2, and lens 4, and is reflected by mirror 5 to ring slit 6 and passes through the annular aperture of the ring slit 6, goes to the left, as seen in FIG. 1, on the optical path 20 after being reflected by a mirror surface of the mirror 8 having the aperture, and is projected into the eye E from external circumferential portions of the pupil of the eye E via the objective lens 9 to illuminate the fundus Ef of the eye E. Light reflected by the fundus Ef passes through the objective lens 9, the central aperture of the mirror 8, the focusing lens 10 and the photographing lens 11, is upwardly reflected by the movable mirror 12 at a position indicated by solid lines, passes through the field lens 14, the mirror 15 and the eyepiece lens 16, and can be observed by an eye e.

In a photographing operation, the movable mirror 12 is retracted from the optical path 30, and the reflecting member 17 is inserted between the condenser lens 2 and the photographing light source 3 by driving the solenoid 18. When the microswitch 19 has confirmed the insertion of the reflecting member 17, the photographing light source 3 is lit. Photographing light from the photographing light source 3 illuminates the fundus Ef of the eye E after passing along the same optical path as the light for observation. Light reflected by the fundus Ef goes to the right, as seen in FIG. 1, and is imaged onto the film 13 through the aperture of a shutter to expose the film 13. At that time, due to the presence of the reflecting member 17, light going to the right, as seen in FIG. 1, from the photographing light source 3 is also reflected by the reflecting member 17, contributing to illumination of the eye E and increasing the amount of the photographing light. After the completion of the photographing operation, the movable mirror 12 returns to the optical path 30, and the reflecting member 17 retracts from the optical path 20. Hence, no problem occurs for another observation of the fundus Ef.

Figure 2:
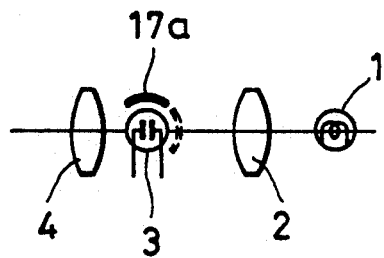
FIG. 2 is a schematic diagram showing the configuration of a part of a fundus camera according to a second embodiment of the present invention.

FIG. 2 is a schematic diagram showing the configuration of a part of a fundus camera according to a second embodiment of the present invention, wherein a reflecting member 17a is rotated around the photographing light source 3. The reflecting member 17a is situated at a side portion of the photographing light source 3 in a retracted state, and is positioned between the photographing light source 3 and the light source 1 for observation by rotating around the photographing light source 3. Hence, the space for arranging the reflecting member 17a becomes compact.

Figure 3:
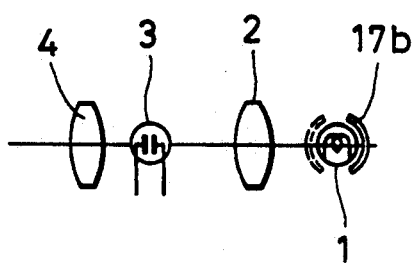
FIG. 3 is a schematic diagram showing a part of a fundus camera according to a third embodiment of the present invention.

FIG. 3 is a schematic diagram showing the configuration of a part of a fundus camera according to a third embodiment of the present invention, wherein a reflecting property is provided for both surfaces of a reflecting member 17b, which is rotated around the light source 1 for observation. During observation operation, the reflecting member 17b is moved to a position indicated by solid lines behind the light source 1 for observation. During a photographing operation, the reflecting member 17b is moved to a position indicated by broken lines between the observation light source 1 and the condenser lens 2. The amount of light incident upon the eye E increases both in observation and photographing operations using this embodiment.

Figure 4:
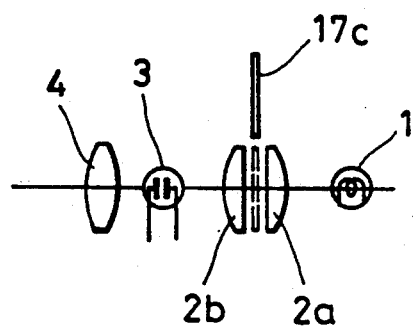
FIG. 4 is a schematic diagram showing a part of a fundus camera according to a fourth embodiment of the present invention.

FIG. 4 is a schematic diagram showing the configuration of a fundus camera according to a fourth embodiment of the present invention. In FIG. 4, a condenser lens 2 comprises two divided condenser lenses 2a and 2b, and a plate-like reflecting member 17c can be inserted between the condenser lenses 2a and 2b. By designing the configuration so that light passing through the condenser lenses 2a and 2b comprises substantially parallel beams, it is unnecessary to make the shape of the reflecting member 17c a curve.

In FIGS. 1-3, although the reflecting effect differs, each of the reflecting members 17a, 17b and 17c does not necessarily have a concave or convex shape, but may have the shape of an inner surface of a cylinder, a plane, an iris stop or a blind shutter. In place of directly confirming the insertion of the reflecting member 17 by a detection means as shown in FIG. 1, the insertion may be confirmed by the movement of the movable mirror 12, a delay circuit, or the like. If a visible-light-cut filter is disposed at a portion closer to the light source 1 for observation than the portion of inserting the reflecting member 17, it is also possible to apply the present embodiments to illumination of a nonmydriatic fundus camera wherein observation is performed by an infrared television camera or the like.

As explained above, in a fundus camera of the present invention, by inserting a reflecting member between a photographing light source and a light source for observation during a photographing operation, illumination brighter than conventional illumination can be obtained when a photographing light source driven by the same power supply is used. Hence, it becomes possible to photograph even the fundus of an eye having a small pupil. If a high-resolution film having low sensitivity is used, it is possible to enlarge the film to a large size, and to observe even fine detail. Hence, the diagnostic capability of such a device increases. The present invention also has the advantages that a photograph having the same density as in the conventional approach can be obtained by a power supply having a smaller size, a lighter weight and a lower cost, and by a photographing light source having, for example, a smaller size, a lower cost and a longer life.

What is claimed is:

1. A fundus camera, comprising:
    a light source for observation;
    an illuminating optical system having a predetermined illuminating optical axis, said light source for observation illuminating a fundus of an eye via said illuminating optical system;
    an observation optical system disposed so as to be able to observe the fundus illuminated by said light source for observation;
    a photographing light source for illuminating the fundus during a photographing operation, said photographing light source being disposed on the illuminating optical axis of said illuminating optical system;
    a photographing system for photographing the fundus illuminated by said photographing light source; and
    a reflecting member disposed between said light source for observation and said photographing light source on the illuminating optical axis so as to reflect light from said photographing light source in the direction of the fundus during illumination by said photographing light source, said reflecting member being retractable from the illuminating optical axis between said light source for observation and said photographing light source.

2. A fundus camera according to claim 1, wherein said reflecting member is rotatable substantially around said light source for observation or said photographing light source.

3. A fundus camera according to claim 1, wherein said reflecting member is configured so as to provide reflecting surfaces on both surfaces thereof, wherein said reflecting member is disposed between said photographing light source and said light source for observation during illumination of the fundus during a photographing operation by said photographing light source, and wherein said reflecting member is disposed at a portion opposite to the direction of illumination of said light source for observation during observation of the fundus by said observation optical system.

4. A fundus camera according to claim 1, further comprising an actuator for inserting said reflecting member between said photographing light source and said light source for observation, and wherein said photographing light source illuminates the fundus while said reflecting member is linked with said actuator.

5. A fundus camera, comprising:
    a light source for observation;
    an illuminating optical system having a predetermined illuminating optical axis, said light source for observation illuminating a fundus of an eye via said illuminating optical system;
    an observation optical system disposed so as to be able to observe the fundus illuminated by said light source for observation;
    a photographing light source for illuminating the fundus during a photographing operation, said photographing light source being disposed on the illuminating optical axis of said illuminating optical system;
    a photographing system for photographing the fundus illuminated by said photographing light source;
    a reflecting member disposed between said light source for observation and said photographing light source on the illuminating optical axis so as to reflect light from said photographing light source in the direction of the fundus during illumination by said photographing light source, said reflecting member being retractable from the illuminating optical axis between said light source for observation and said photographing light source; and
    a detector for confirming the insertion of said reflecting member between said photographing light source and said light source for observation.

6. A fundus camera according to claim 5, wherein said photographing light source illuminates the fundus after said detector has detected the insertion of said reflecting member between said photographing light source and said light source for observation.

7. A fundus camera, comprising:
    a light source for observation;
    an illuminating optical system having a predetermined illuminating optical axis, said light source for observation illuminating a fundus of an eye via said illuminating optical system;
    an observation optical system disposed so as to be able to observe the fundus illuminated by said light source for observation;
    a photographing light source for illuminating the fundus during a photographing operation, said photographing light source being disposed on the illuminating optical axis of said illuminating optical system;

a photographing system for photographing the fundus illuminated by said photographing light source; and a reflecting member disposed between said light source for observation and said photographing light source on the illuminating optical axis so as to reflect light from said photographing light source in the direction of the fundus during illumination by said photographing light source, said reflecting member being retractable from the illuminating optical axis between said light source for observation and said photographing light source, wherein said reflecting member includes a concave spherical reflecting surface.

8. A fundus camera according to claim 1, wherein said reflecting member includes a plane-like reflecting surface, and wherein said illuminating optical system includes an optical member for illuminating said plane-like reflecting surface while converting light from said photographing light source into parallel light beams when said reflecting member is inserted between said photographing light source and said light source for observation.

9. A fundus camera according to claim 1, wherein said light source for observation and said photographing light source are on the optical axis of said illumination optical system.

10. An ophthalmic photographing apparatus, comprising:

a light source for observation;

an illuminating optical system having a predetermined illuminating optical axis, said light source for observation illuminating a predetermined portion of an eye to be inspected via said illuminating optical system;

an observation optical system disposed so as to be able to observe the predetermined portion of the eye illuminated by said light source for observation;

a photographing light source for illuminating the predetermined portion of the eye during a photographing operation, said photographing light source being disposed on the illuminating optical axis of said illuminating optical system;

a photographing system for photographing the predetermined portion of the eye illuminated by the photographing light source; and a reflecting member disposed between said light source for observation and said photographing light source on the illuminating optical axis so as to reflect light from said photographing light source in the direction of the eye during illumination by said photographing light source, said reflecting member being retractable from said illuminating optical axis between said light source for observation and said photographing light source.

11. An apparatus according to claim 10, further comprising an actuator for inserting said reflecting member between said photographing light source and said light source for observation, and wherein said photographing light source illuminates the predetermined portion of the eye while said reflecting member is linked with said actuator.

12. An apparatus according to claim 9, wherein said light source for observation and said photographing light source are on the optical axis of said illumination optical system.

* * * * *

UNITED STATES PATENT AND TRADEMARK OFFICE
CERTIFICATE OF CORRECTION

PATENT NO. : 5,300,964
DATED : April 5, 1994
INVENTOR(S) : KAZUNOBU KOBAYASHI

It is certified that error appears in the above-indentified patent and that said Letters Patent is hereby corrected as shown below:

On the title page, item:
[57] ABSTRACT
    Line 2, "illiminating" should read --illuminating--.
    Line 3, "illiminating" should read --illuminating--.
    Line 4, "illiminates" should read --illuminates--.
    Line 5, "liminating" should read --luminating--.
    Line 7, "illiminated" should read --illuminated--.
    Line 8, "illiminat-" should read --illuminat- --.
  Line 10, "illiminating" should read --illuminat- --; and
      "illiminating" should read --illuminating--.

COLUMN 1
    Line 67, "illiminating" should read --illuminating--.

COLUMN 2
    Line 53, "illiminating" should read --illuminating--.
    Line 54, "illiminating" should read --illuminating--.
    Line 55, "illiminating" should read --illuminating--.
    Line 58, "illiminated" should read --illuminated--.
    Line 59, "illiminating" should read --illuminating--.
    Line 64, "illiminated" should read --illuminated--.
    Line 67, "illiminating" should read --illuminating--.

UNITED STATES PATENT AND TRADEMARK OFFICE
CERTIFICATE OF CORRECTION

PATENT NO. : 5,300,964
DATED : April 5, 1994
INVENTOR(S) : KAZUNOBU KOBAYASHI

It is certified that error appears in the above-indentified patent and that said Letters Patent is hereby corrected as shown below:

COLUMN 3
Line 1, "illimina-" should read --illumina- --.
Line 9, "illiminates" should read --illuminates--.
Line 67, "optical path 01" should read -- optical path 20 --.

COLUMN 8
Line 31, "claim 9, should read --claim 10,--.

Signed and Sealed this

Eleventh Day of October, 1994

Attest:

BRUCE LEHMAN

Attesting Officer

Commissioner of Patents and Trademarks